United States Patent
Rowe et al.

(10) Patent No.: US 6,692,910 B2
(45) Date of Patent: Feb. 17, 2004

(54) INHIBITION OF A TARGET MESSENGER RNA WITH A MODIFIED U1 SMALL NUCLEAR RNA

(75) Inventors: David W. Rowe, West Hartford, CT (US); Mary Louise Stover, So. Glastonbury, CT (US); Akin Beckley, West Hartford, CT (US)

(73) Assignee: The University of Connecticut, Farmington, CT (US)

(*) Notice: Subject to any disclaimer, the term of this patent is extended or adjusted under 35 U.S.C. 154(b) by 161 days.

(21) Appl. No.: 09/123,064

(22) Filed: Jul. 27, 1998

(65) Prior Publication Data

US 2003/0082149 A1 May 1, 2003

Related U.S. Application Data

(60) Provisional application No. 60/053,998, filed on Jul. 28, 1997.

(51) Int. Cl.$^7$ .......................... C12Q 1/68; C07H 21/00
(52) U.S. Cl. .......................... 435/6; 435/325; 435/375; 435/91.1; 536/23.1; 536/24.5
(58) Field of Search .................. 435/6, 91.1, 91.3, 435/375, 325; 536/231, 23.2, 24.5, 24.3, 24.31, 24.33; 514/44

(56) References Cited

U.S. PATENT DOCUMENTS

| | | | |
|---|---|---|---|
| 4,511,713 A | 4/1985 | Miller et al. | |
| 5,190,931 A | 3/1993 | Inouye | |
| 5,272,065 A | 12/1993 | Inouye et al. | |
| 5,583,035 A | 12/1996 | Kretschmer et al. | |
| 5,624,803 A | 4/1997 | Noonberg et al. | |
| 5,814,500 A | * 9/1998 | Dietz | 435/455 |
| 5,994,124 A | * 11/1999 | Bozzoni | |

FOREIGN PATENT DOCUMENTS

| | | |
|---|---|---|
| EP | 0601585 A2 | 6/1994 |
| WO | WO93/24133 | 12/1993 |
| WO | WO95/06718 | 3/1995 |
| WO | WO95/06744 | 3/1995 |

OTHER PUBLICATIONS

Agrawal, "Antisense oligonucleotides: towards clinical trials" TIBTECH, Vol 14, p 376–387, Oct. 1996.*
Branch, "A good antisense molecule is hard to find", TIBS23, p 45–50, Feb. 1998.*
Crooke, Antisense Research and Application, Springer, New York, p1–50, Jul. 1998.*
Miller et al., "Improved Retroviral Vectors for Gene Transfer and Expression" Bio Techniques, vol. 7, No. 9, 1989.*
Montgomery, R.A. and Dietz, H.C., "Inhibition of fibrillin 1 expression using U1 snRNA as a vehicle for the presentation of antisense targeting sequence", *Human Molecular Genetics*, 6(4):519–525 (1997).

Zhuang, Y. and Weiner, A.M., "A Compensatory Base Change in U1 snRNA Suppresses a 5' Splice Site Mutation", *Cell*, 46:827–835 (1986).
Cohen, J.B., et al., "U1 Small Nuclear RNAs with Altered Specificity Can Be Stably Expressed in Mammalian Cells and Promote Permanent Changes in Pre–mRNA Splicing", *Mol. Cell. Biol.*, 13(5):2666–2676 (1993).
Furth, P.A., et al., "Sequences Homologous to 5' Splice Sites Are Required for the Inhibitory Activity of Papillomavirus Late 3' Untranslated Regions", *Mol. Cell. Biol.*, 14(8):5278–5289 (1994).
Barksdale S.K. and Baker, C.C., "The Human Immunodeficiency Virus Type 1 Rev Protein and the Rev–Responsive Element Counteract the Effect of an Inhibitory 5' Splice Site in a 3' Untranslated Region", *Mol. Cell. Biol.*, 15(6):2962–2971 (1995).
Michienzi, A., et al., "U1 small nuclear RNA chimeric ribozymes with substrate specificity for the Rev pre–mRNA of human immunodeficiency virus", *Proc. Natl. Acad. Sci. USA*, 93:7219–7224 (1996).
Konforti, B.B., et al., "Disruption of Base Pairing between the 5' Splice Site and the 5' End of U1 snRNA Is Required for Spliceosome Assembly", *Cell*, 75:863–873 (1993).
Nandabalan, K., et al., "Mutations in U1 snRNA Bypass the Requirement for a Cell Type–Specific RNA Splicing Factor", *Cell*, 73:407–415 (1993).
Nesic, D. and Maquat, L.E., "Upstream introns influence the efficiency of final intron removal and RNA 3'–end formation", *Genes Devel.*, 8:363–375 (1994).
Lund, E. and Dahlberg, J.E., "True Genes for Human U1 Small Nuclear RNA", *J. Biol. Chem.*, 259(3):2013–2021 (1984).
Durland, R.H., et al., "Binding of Triple Helix Forming Oligonucleotides to Sites in Gene Promoters", *Biochemistry*, 30(38):9246–9255 (1991).
Duval–Valentin, G., et al., "Specific inhibition of transcription by triple helix–forming oligonucleotides", *Proc. Natl. Acad. Sci. USA*, 89:504–508 (1992).
Hélène, C., "The anti–gene strategy: control of gene expression by triplex–forming–oligonucleotides", *Anti–Cancer Drug Design*, 6:569–584 (1991).
Coleman, J., et al., "The Use of RNAs Complementary to Specific mRNAs to Regulate the Expression of Individual Bacterial Genes", *Cell*, 37:429–436 (1984).
Terns, M.P., et al., "Multiple cis–acting signals for export of pre–U1 snRNA from the nucleus", *Genes and Development*, 7:1898–1908 (1993).

* cited by examiner

*Primary Examiner*—Andrew Wang
*Assistant Examiner*—James Douglas Schultz
(74) *Attorney, Agent, or Firm*—Cummings & Lockwood

(57) ABSTRACT

Methods of reducing gene expression, protein production and messenger RNA output in a cell are disclosed. Also disclosed is a method for delivering a selected ribozyme to a target mRNA in a cell. The methods are useful for prophylactic and therapeutic purposes.

3 Claims, 6 Drawing Sheets

U1 snRNA Construct

SEQUENCE LISTING

```
<160> NUMBER OF SEQ ID NOS:  9

<210> SEQ ID NO 1
<211> LENGTH: 10
<212> TYPE: DNA
<213> ORGANISM: Homo Sapien

<400> SEQUENCE: 1
tacttacctg                                                          10

<210> SEQ ID NO 2
<211> LENGTH: 10
<212> TYPE: DNA
<213> ORGANISM: Homo Sapien

<400> SEQUENCE: 2
caggtaagta                                                          10

<210> SEQ ID NO 3
<211> LENGTH: 29
<212> TYPE: DNA
<213> ORGANISM: Oligonucleotide

<400> SEQUENCE: 3
ggcccaagat ctcatactta cctggcagg                                     29

<210> SEQ ID NO 4
```

```
<211> LENGTH: 29
<212> TYPE: DNA
<213> ORGANISM: Oligonucleotide

<400> SEQUENCE: 4
ggcccaagat ctcagatgaa cctggcagg                                      29

<210> SEQ ID NO 5
<211> LENGTH: 28
<212> TYPE: DNA
<213> ORGANISM: Oligonucleotide

<400> SEQUENCE: 5
cagtgccaag cttgcatgcc tgcaggtc                                       28

<210> SEQ ID NO 6
<211> LENGTH: 28
<212> TYPE: DNA
<213> ORGANISM: Oligonucleotide

<400> SEQUENCE: 6
cagtgccaag cttgcatgcc agcaggtc                                       28

<210> SEQ ID NO 7
<211> LENGTH: 10
<212> TYPE: DNA
<213> ORGANISM: Artificial Sequence
<220> FEATURE:
<223> OTHER INFORMATION: Sequence from the U1:CAT570 construct

<400> SEQUENCE: 7
caggttcatc                                                           10

<210> SEQ ID NO 8
<211> LENGTH: 10
<212> TYPE: DNA
<213> ORGANISM: Artificial Sequence
<220> FEATURE:
<223> OTHER INFORMATION: Sequence from the U1:beta-gal construct

<400> SEQUENCE: 8
cagttctgta                                                           10

<210> SEQ ID NO 9
<211> LENGTH: 10
<212> TYPE: DNA
<213> ORGANISM: Artificial Sequence
<220> FEATURE:
<223> OTHER INFORMATION: Sequence from the U1:eGFP construct

<400> SEQUENCE: 9
ccgacaagca                                                           10
```

INHIBITION OF A TARGET MESSENGER RNA WITH A MODIFIED U1 SMALL NUCLEAR RNA

RELATED APPLICATIONS

This application claims priority to U.S. Provisional Application No. 60/053,998, filed Jul. 28, 1997, the contents of which are incorporated herein by reference in their entirety.

GOVERNMENT SUPPORT

This invention was supported, in whole or in part, by Grant No. AR30426 from the National Institutes of Health. The United States Government has certain rights in this invention.

BACKGROUND OF THE INVENTION

Gene expression can be regulated at the post transcriptional level. For example, antisense RNA strategies have received great attention as a means for gene regulation. Antisense constructs, either in the form of oligonucleotides or as expressed antisense ribonucleic acids (RNAs), form colinear hybrids with target messenger ribonucleic acid (mRNA). In forming a double-stranded region on the mRNA, subsequent steps of protein synthesis may be interrupted by any of a variety of mechanisms. Interruption may occur by sterically blocking ribosome assembly or progression, sterically blocking intron/exon junctions and splice-sites needed for the processing of premature mRNA, or by invoking the cellular enzyme RNAse H that specifically cleaves mRNA in mRNA/DNA hybrids. However, the overall efficiency of antisense inhibition is quite variable and requires empirically testing a variety of constructs to obtain satisfactory results. Furthermore, it is often difficult to show an effect in stably transfected cells.

Ribozymes, RNA molecules that possess self-catalytic activity, have the theoretical advantage over antisense RNA strategies as a means for gene regulation because they are able to bind and cleave a target mRNA, dissociate, then find, bind and cleave another target mRNA. The specific target cleavage sites have a sequence requirement (Symons, *Ann. Rev. Biochem.*, 61:641–671 (1992)). However, although ribozymes work well in vitro, their effectiveness in vivo has been limited.

Reduction of mRNA output from a gene has increasing importance in the development of strategies for somatic gene therapy as well as a molecular tool to study the function of a gene. Thus, there is a continued need to develop new and improved methods for gene regulation at the transcriptional level.

SUMMARY OF THE INVENTION

The present invention relates to the use of a mutant or modified U1 small nuclear ribonucleic acid (U1 snRNA) to regulate, reduce or inhibit gene expression in cells. Gene expression in a cell in accordance with the present invention is regulated, reduced or inhibited by introducing into the cell a mutant U1 snRNA which binds or hybridizes to a preselected site having a particular RNA sequence within a mRNA produced by a gene located in the cell. Upon binding to or hybridization with the preselected site, the mRNA becomes sequestered within the nucleus and as a result, the protein coded for by the mRNA is not produced.

Thus, in one embodiment, the invention is directed to a method of reducing expression of a gene in a cell comprising introducing into the cell a mutant U1 snRNA which binds to a preselected site in a mRNA produced by the gene. In a second embodiment, the invention is directed to a method of reducing protein production in a cell comprising introducing into the cell a mutant U1 snRNA which binds to a preselected site in a mRNA that codes for the protein. In a third embodiment, the invention is directed to a method of reducing output in a cell of a mRNA produced by a gene located in the cell comprising introducing into the cell a mutant U1 snRNA which binds to a preselected site in the mRNA.

The invention also relates to a method of delivery of a selected ribozyme to a target mRNA in a cell comprising introducing into the cell a ribozyme-U1 snRNA complex.

The invention further relates to a method of reducing expression of a gene in a human comprising (a) obtaining a biological sample containing cells from the human and maintaining the cells under conditions appropriate for cell viability; (b) introducing into the cells a mutant U1 snRNA which binds to a preselected site in a mRNA produced by the gene; and (c) returning the cells obtained in step (b) to the human.

The invention still further relates to methods for treating and/or prophylaxis of viral infections (e.g., human immunodeficiency virus (HIV) infection), dominant negative inherited diseases and disorders, and cancer due to overexpression of a cancer gene, in a human in need thereof. In one embodiment of this aspect of the invention, the method comprises (a) obtaining a biological sample containing cells from the human and maintaining the cells under conditions appropriate for cell viability; (b) introducing into the cells a mutant U1 snRNA which binds to a preselected site in a mRNA produced by a targeted gene; (c) maintaining the cells from step (b) under conditions appropriate for the mutant U1 snRNA to bind to the preselected site; and (d) returning the cells obtained in step (c) to the human. In a second embodiment of this aspect of the invention, the method comprises (a) obtaining a biological sample containing cells from the human and maintaining the cells under conditions appropriate for cell viability; (b) introducing into the cells a ribozyme-U1 snRNA complex comprising a selected ribozyme which is capable of cleaving a mRNA produced by a targeted gene and which is covalently linked to the 5' end of a U1 snRNA; (c) maintaining the cells from step (b) under conditions appropriate for the selected ribozyme to cleave the mRNA; and (d) returning the cells obtained in step (c) to the human. In both embodiments of this aspect of the invention, the targeted gene is selected because its expression leads to undesirable and detrimental effects in the human (e.g., acquired immunodeficiency syndrome (AIDS), dominant negative inherited disease, cancer), thereby making it desirable to regulate, reduce or inhibit expression of the selected gene.

In a particular embodiment, a method for treating and/or prophylaxis of a viral infection, such as a HIV infection, in a human in need thereof comprises (a) obtaining a biological sample containing cells from the human and maintaining the cells under conditions appropriate for cell viability; (b) introducing into the cells a ribozyme-U1 snRNA complex comprising a selected ribozyme which is capable of cleaving a target viral mRNA and which is covalently linked to the 5' end of a U1 snRNA; (c) maintaining the cells from step (b) under conditions appropriate for the selected ribozyme to cleave the target viral mRNA; and (d) returning the cells obtained in step (c) to the human. In a particular embodiment, the method for treating and/or prophylaxis of a HIV infection further comprises introducing into the cells a mutant U1 snRNA which binds to a preselected site in the 3' long terminal repeat (LTR) proximal to the polyadenylation (PA) site (the 3' terminal exon on the viral protein).

In a yet another embodiment of the invention, the methods of the present invention further comprise introducing into the cells a second or multiple mutant U1 snRNA, wherein each mutant U1 snRNA binds to a different preselected site in a mRNA produced by the same targeted gene.

The invention also includes compositions comprising a mutant U1 snRNA which binds to a preselected site in a mRNA produced by a gene in a cell and compositions comprising a ribozyme-U1 snRNA complex.

The invention further relates to methods of producing the compositions of the present invention. In two particular embodiments, the invention relates to methods of producing compositions comprising a mutant U1 snRNA which binds to a preselected site in a mRNA produced by a targeted gene in a cell and to methods of producing compositions comprising a ribozyme-U1 snRNA complex. The compositions of the invention can be prepared by selecting a non-consensus donor site in a mRNA produced by a target gene for binding the mutant U1 snRNA and then modifying the 5'-TACTTACCTG-3' (SEQ ID NO: 1) sequence at the 5' end of the U1 snRNA so that it is complementary to the non-consensus donor site selected. In the case of a ribozyme-U1 snRNA complex, the 5'-TACTTACCTG-3' (SEQ ID NO: 1) sequence at the 5' end of the U1 snRNA is modified so that it incorporates the ribozyme selected to be delivered to a mRNA produced by a target gene in a cell.

The invention also includes nucleic acid molecules which encode the mutant U1 snRNA of the invention. Also envisioned are host cells which comprise the nucleic acid molecules of the invention.

In one embodiment of the invention, the preselected site is located in a terminal exon of the mRNA. In a particular embodiment, the terminal exon is a 3' terminal exon of the mRNA.

In another embodiment of the invention, the preselected site is located in an internal exon of the mRNA. In a particular embodiment of the invention, the mutant U1 snRNA and ribozyme-U1 snRNA complex are encoded by a DNA.

DETAILED DESCRIPTION OF THE INVENTION

Figure 1:
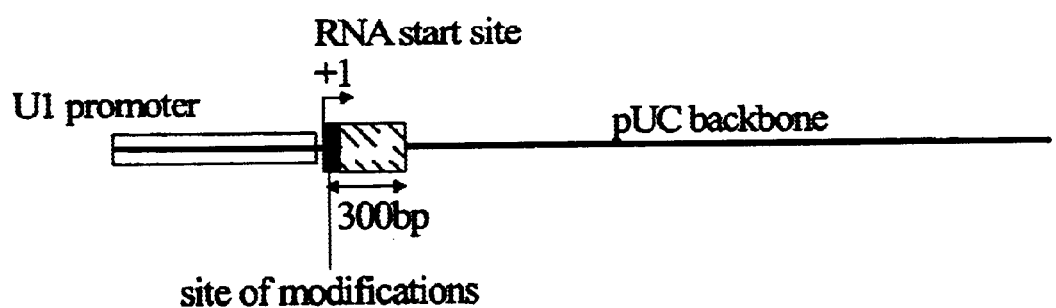
FIG. 1 is a genetic map of a U1 snRNA construct.

The cis elements within an RNA transcript that are required for splicing include the 5' splice donor signal, the sequence surrounding the branch point and the 3' splice acceptor signal. Interacting with these three RNA landmarks are small nuclear RNAs (snRNA) and associated nuclear proteins (snRNP) that form the splicesosome.

The first step of the splicing reaction involves the binding of U2 snRNA to the branch point (Smith et al., *Mol. Cell Biol.* 13:4939–4952 (1993)). Subsequently, U1 snRNA binds the U2 complex and scans in a 5'->3' direction for the first acceptable donor sequence. In many cases, the limit of the scanning is approximately 300 bp. The U1 snRNA binds to the 5' donor site with the aid of two snRNPs identified as hnRNPA1 and ASF/SF2. The relative proportion of these proteins can determine which of two potential 5' donor sites are selected and situations have been described where these two proteins act in a competitive manner (Sun et al., *Genes & Develop.* 7:2598–2608 (1993), and Kohtz et al., *Nature* 368:119–124 (1994)). These proteins appear to recognize a composite of a consensus donor site and a donor/acceptor site, respectively. When studied in in vitro splicing systems, the complex of the 5' donor site, 3' acceptor site and associated proteins is called a pre-splicesosome. The process of identifying exons by their 5' acceptor, 3' donor borders have been developed by Berget as a concept of exon definition (Berget, *J. Biol. Chem.* 270(6):2411–2414 (1995)). This model has recently been modified to explain exons smaller than 40 bp in length (Talerico et al., *Mol. Cell Biol.* 14:3434–3445 (1994)).

In the next step of the splicing reaction, the ends of the two exons are approximated probably by hybridization of the AG of the acceptor sequence to U1 snRNA (Newman, *Curr. Opin. Cell Biol.* 6:360–367 (1994)). Prebound U4/U6 snRNA joins the complex. With the dissociation of U4 from the critical U4/U6 snRNA complex, U6 snRNA is activated to control the remaining step of the splicing reaction. Initially, U1 snRNA leaves the splicesosome complex being replaced by U5 snRNA to hold the two exons in close proximity (Sontheimer et al., *Science* 262:1989–1995 (1993)). The binding of a conserved sequence (ACAGAG) within U6 snRNA is essential for displacing U1 snRNA from the splicesosome complex (Konforti et al., *Cell* 75:863–873 (1993)) probably through hybridization of the ACA to +4 to +6 position of the splice donor site. Once in position, U6 snRNA provides the environment for the branch point A to cleave the donor site thereby forming the lariat (Kandels-Lewis et al., *Science* 262:2035–2039 (1993)).

The final step of the splicing reaction occurs when GAG of the conserved U6 snRNA sequence binds the splice acceptor sequence through non-Watson/Crick binding and provides the environment for the terminal G of the upstream exon to cleave the acceptor site and ligate the two exons (Sun et al., *Genes & Develop.* 9:843–854 (1995)).

The determinants of an adequate 5' donor sequence are only partially understood. The greater the hybridization strength of the 5' sequences of U1 RNA to the donor site the more likely such a site will be selected (Lear et al., *J. Mol. Biol.* 211:103–115 (1990)). However, a great variation in donor site selection occurs in nature. Donor site selection is thought to be determined by factors such as the relative balance of its two binding proteins and whether there is secondary structure within the RNA which might hide a donor site from its complement (Goguel et al., *Mol. Cell Biol.* 13:6841–6848 (1993)).

An unusual situation arises when two exons occur within 40 nucleotides of one another (Eperon et al., *EMBO J.* 12(9):3607–3617 (1993)). If both sites bind U1 snRNA and start to form a splicesosome, then the entire splicing process of that RNA is inhibited. If the two closely spaced donors are of an unequal strength, then the one with the greater strength will be preferentially utilized.

However, factors other than the donor site also determine which exons will be recognized. For example, purine rich sequences within exons seem to participate in exon recognition by binding to a snRNP and strengthening the 3' splice site (Watakabe et al., *Genes & Develop.* 7:407–418 (1993); and Dominski et al., *Mol. Cell Biol.* 14:7445–7454 (1994)). Premature stop codons within exons but distinct from recognized splice signals have been found to be responsible for exon skipping (Dietz et al., *Nature Genetics* 8:183–188 (1994); and Lozano et al., *EMBO J.* 13:4617–4622 (1994)). Finally, there are long range influences, such as the strength of upstream splice units, which also have influence on whether an exon will be recognized or will undergo exon skipping because of inadequate recognition by the splicing machinery (Goguel et al., *Cell* 72:893–901 (1993)).

Polyadenylation is a necessary step for nuclear export of mRNA. The primary transcript from most genes extends for 1–4 kb 3' of the translation stop signal prior to transcriptional termination. Sequences within the untranslated 3' sequence determine where the closely coupled processes of endonucleolyic cleavage and polyadenylation will occur (Wahle E. et al., *Ann. Rev. Biochem.* 61:419–440 (1992)). The polyadenylation signal (AAUAAA) is central to this step as well as U-rich and G-rich sequences both 5' and 3' of the cleavage site (Tantravahi et al., *Mol. Cell Biol.* 13:578–587 (1993); and Bagga et al., *Nuc. Acids Res.,* 23(9):1625–1631 (1995)). It appears that U1 snRNP can effect polyadenylation in a positive manner, although not through a consensus donor site (Lutz et al., *Genes & Develop.* 9:576–586 (1994)). Recent studies point to the importance of a well defined splice unit preceding the terminal exon (Niwa et al., *Nature* 360:277–280 (1992)) and the deleterious effect of an unpaired splice donor in the terminal exon on efficient polyadenylation and export of the RNA (Nesic et al., *Genes & Develop.* 8:363–375 (1994)).

Significant progress in understanding mRNA transport through the nucleus has been made (Baskin, *Science* 268:1564–1656 (1995)). The processes of transcription and splicing appear to occur simultaneously (Wuarin et al., *Mol. Cell Biol.* 14:7219–7225 (1994)) in close association with the nuclear matrix (Blencowe et al., *J. Cell Biol.* 127:593–607 (1994); and Zeng et al., *Proc. Natl. Acad. Sci. USA* 91:1505–1509 (1994)). Tracts of RNA have been visualized originating from the site of transcription and are thought to represent the pathway along which splicing is progressing (Carter et al., *Science* 259:1330–1335 (1993); Xing, et al., *Science* 259:1326–1330 (1993)). Numerous reports indicate that incompletely spliced mRNAs (Zachar et al., *J. Cell Biol.* 121:729–742 (1993)) or RNA with partially formed splicesosome complexes are retained within the nuclear compartment probably still attached to the nuclear matrix (Legrain et al., *Cell* 57:573–583 (1989)).

A second requirement for nuclear export is that the spliced mRNA must have its translation termination codon in the same exon as the polyadenylation signal. Mutations which produce a premature stop codon in all but the terminal exon are associated with low cytoplasmic levels of the product (Connor et al., *J. Biol. Chem.* 269:25178–25184 (1994)). At one time it was felt that the premature stop codon resulted in a nonfunctional truncated protein. However, in most cases studied with modern molecular techniques, the RNA is not transported to the cytoplasmic compartment when the stop codon occurs in any exon except the terminal exon (Cheng et al., *Mol. Cell Biol.* 13(3):1892–1902 (1993)).

Nuclear export is a controlled process, probably regulated by specific binding proteins (Fabre et al., *Cell* 78:275–289 (1994)) that shuttle between the nuclear matrix and the nuclear membrane (Huang et al., *J. Cell Biol.* 126:877–899 (1994); and Mehlin et al., *J. Cell Biol.* 129:1205–1216 (1995)). At this point, it is not known if these proteins play a role in retaining a mRNA with a premature stop, but mutations in the binding proteins cause clustering of ribonuclear complexes at the nuclear pores (Gorsch et al., *J. Cell Biol.* 129:939–955 (1995)).

For a review of the post-transcriptional mechanisms of gene regulation see, e.g., Moore et al., *In: The RNA World: The Nature of Modern RNA Suggests a Prebiotic RNA World*, Gesteland et al., Eds., Cold Spring Harbor Laboratory Press, Cold Spring Harbor, N.Y., pp.303–357 (1993); and Nilsen, *Cell,* 78:1–4 (1994).

A U1 snRNA directed to the sequence homologous to bases −2 through +3 of a classic donor site without homology to the U6 sequence at position +4 to +6 can allow U1 snRNA to bind with assistance from U1 snRNP. However, splicesosome progression does not occur because endogenous U6 cannot compete with the mutant U1 snRNA for its binding site. Such a design can lead to a RNA tethered to the nuclear matrix without further splicing.

A second U1 snRNA which has limited homology to an authentic donor, particularly at bases −2 to +3, but identity with +4 to +6, can lead to the progression of splicing to an authentic acceptor site and to completion but yield an aberrantly spliced product.

It has now been demonstrated that the splicing process is disrupted when U1 snRNA binds a 3' terminal exon within a mRNA. Due to the absence of an appropriately paired acceptor site, the U1 snRNA cannot be displaced from the terminal exon by a U6 snRNA. Consequently, the mRNA is sequestered within the nucleus, and as a result, protein output is dramatically reduced.

Thus, it has now been demonstrated that expression of a target gene in a cell can be regulated, reduced or inhibited by altering the nucleic acid sequence of a U1 snRNA gene so that the U1 snRNA no longer binds to the splice donor site sequence (CAGGTAAGTA) (SEQ ID NO:2) that it uses to initiate splicing of the target gene but, instead binds to a non-consensus donor site sequence that is unrelated to splicing of the target gene.

As a result, a method is provided herein to reduce expression of a gene in a cell comprising introducing into the cell a mutant (or modified) U1 snRNA which binds or hybridizes to a preselected site having a particular RNA sequence within a mRNA produced by the gene.

The present invention also provides a method for reducing protein production in a cell comprising introducing into the cell a mutant U1 snRNA which binds to a preselected site in a mRNA coding for the protein. The present invention further provides a method of reducing output in a cell of a mRNA produced by a gene located in the cell comprising introducing into the cell a mutant U1 snRNA which binds to a preselected site in the mRNA.

A method is also provided herein for delivering selected ribozymes to a target mRNA in a cell comprising introducing into the cell a ribozyme-U1 snRNA complex. As used herein, the term "ribozyme-U1 snRNA complex" refers to a complex which includes a selected ribozyme covalently linked to the 5' end of a U1 snRNA.

In a particular embodiment, the methods of the present invention further comprise introducing into the cells a second or multiple mutant U1 snRNA, wherein each mutant U1 snRNA binds to a different preselected site in a mRNA produced by a particular target gene. The present invention also includes methods wherein a second or multiple mutant U1 snRNA binds to a different preselected site in a mRNA produced by different target genes.

The methods of the present invention can complement other methods (e.g., antisense, ribozyme) for reducing mRNA output since the present invention operates by a fundamentally different molecular mechanism.

U1 snRNA is expressed by a polymerase II promoter and is present in most eukaryotic cells, including human, rodent, chicken, fruit fly, frog, sea urchin and dinoflagellate cells (Lund et al., *J. Biol. Chem.*, 259(3):2013–2021 (1984)). The RNA is exported to the cytoplasm where the 5' cap is hypermethylated, the 3' end modified and binding to Sm proteins occurs prior to its reentry to the nucleus (Terns et al., *Genes & Develop.*, 7:1898–1908 (1993)).

The terms "mutant U1 snRNA" and "modified U1 snRNA", as used herein, refer to a U1 snRNA that has been modified so that it no longer recognizes the splice donor site sequence (CAGGTAAGTA) (SEQ ID NO:2) (Cohen et al., *Mol. Cell. Biol.*, 13:2666–2676 (1993); and Cohen et al., *Proc. Natl. Acad. Sci. USA*, 91:10470–10474 (1994)) that it uses to initiate the splicing process of a target gene. That is, a mutant U1 snRNA is a U1 snRNA which has been modified so that it no longer binds to the splice donor site sequence (CAGGTAAGTA) (SEQ ID NO: 2) based on complementarity of the donor site sequence with sequence at the 5' end of the U1 snRNA. Instead, the mutant U1 snRNA is designed so that it recognizes a preselected site having a unique RNA sequence within a target mRNA produced by a target gene that is unrelated to splicing of the gene. "Preselected site", as used herein, refers to a site having a particular RNA sequence in a mRNA which has been selected as the non-consensus donor site (target site) for binding the mutant U1 snRNA. Thus, the mutant U1 snRNA is a U1 snRNA which has been modified so that its 5' end recognizes a non-consensus donor site sequence (a sequence unrelated to the splicing process) within the mRNA of a target gene. As a result, the mutant U1 snRNA binds to the non-consensus donor site sequence based on complementarity of the non-consensus donor site sequence with sequence at the 5' end of the mutant U1 snRNA. Binding of a mutant U1 snRNA to a non-consensus donor site sequence within the target mRNA suspends the target mRNA within the splicing machinery, thereby preventing its further maturation. Thus, as defined herein, a mutant or modified U1 snRNA includes a ribozyme-U1 snRNA complex.

The mutant U1 snRNAs of the present invention are designed by (a) selecting a non-consensus donor site (target site) in the mRNA (produced by a target gene) for binding the mutant U1 snRNA (the preselected site); and (b) modifying the 5'-TACTTACCTG-3' (SEQ ID NO: 1) sequence at the 5' end of the U1 snRNA so that it is complementary to the non-consensus donor site selected in (a). In a particular embodiment, the preselected site is located in a terminal exon of the target mRNA. The terminal exon can be a 3' terminal exon or a 5' terminal exon of the target mRNA. In another embodiment, the preselected site is located in an internal exon of the target mRNA. In addition, the preselected site can be located in an untranslated and/or polymorphic region of the target mRNA.

In the case of a ribozyme-U1 snRNA complex, the complex is designed by (a) selecting a ribozyme to be delivered to the mRNA produced by a target gene in a cell (selected ribozyme); and (b) modifying the 5'-TACTTACCTG-3' (SEQ ID NO: 1) sequence at the 5' end the U1 snRNA so that it incorporates the ribozyme selected in (a).

The mutant U1 snRNAs of the present invention can be manufactured according to methods generally known in the art. For example, the mutant U1 snRNAs can be manufactured by chemical synthesis or recombinant DNA/RNA technology (see, e.g., Cohen et al, *Mol Cell. Biol.*, 13(5) :2666–2676 (1993); Sambrook et al., Eds., *Molecular Cloning, A Laboratory Manual*, 2nd edition, Cold Spring Harbor University Press, New York, 1989; and Ausubel et al, Eds., *Current Protocols In Molecular Biology*, John Wiley & Sons, New York, 1994–1997). As discussed above, the mutant U1 snRNAs, designed and manufactured as described herein, do not bind to the splice donor site sequence (CAGGTAAGTA)(SEQ ID NO:2).

As used herein, "cell" refers to a eukaryotic cell. Typically, the cell is of animal origin and can be a stem cell or somatic cells. Suitable animal cells can be of, for example, mammalian and avian origin. Examples of mammalian cells include human, bovine, ovine, porcine, murine, rabbit cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

Typically, cells isolated from a specific tissue (such as epithelium, fibroblast or hematopoietic cells) are categorized as a "cell-type." The cells can be obtained commercially or from a depository or obtained directly from an animal, such as by biopsy. Alternatively, the cell need not be isolated at all from the animal where, for example, it is desirable to deliver the vector to the animal in gene therapy.

A gene encoding a mutant U1 snRNA of the present invention can be introduced into a cell by a variety of methods. As a first step, the gene encoding the mutant U1 snRNA can be inserted into a nucleic acid vector, e.g., a DNA vector, such as a plasmid, virus or other suitable replicon (e.g., a viral vector), which can be present in a single copy or multiple copies, or the gene can be integrated in the cell chromosome. Such a suitable replicon contains all or part of the coding sequence for the mutant U1 snRNA operably linked to one or more expression control sequences whereby the coding sequence is under the control of transcription signals to permit production or synthesis of the mutant U1 snRNA. Such expression control sequences include promoter sequences, enhancers, and transcription binding sites. Selection of the promoter will generally depend upon the desired route for expressing mutant U1 snRNA. In a preferred embodiment, the promoter is the native U1 snRNA promoter. In another embodiment, the promoter is the U6 snRNA promoter.

Where the mutant U1 snRNA will be transformed into a cell by a viral vector, preferred promoter sequences include viral, such as retroviral or adenoviral promoters. Preferred promoters include the native U1 snRNA and U6 snRNA promoters. Other examples of suitable promoters include the cytomegalovirus immediate-early promoter, the retroviral LTR, SV40, and TK promoter.

The elements which comprise the nucleic acid molecule can be isolated from nature, modified from native sequences or manufactured de novo, according to methods known in the art. The elements can then be isolated and fused together by methods known in the art, such as exploiting and manufacturing compatible cloning or restriction sites.

As a second step, the vector can be introduced into a cell by a method appropriate to the type of cell (e.g., transformation, transfection). Examples of suitable methods of transfecting or transforming cells include calcium phosphate precipitation, electroporation, microinjection, infection, lipofection and direct uptake. Such methods are described in more detail, for example, in Sambrook et al., *Molecular Cloning: A Laboratory Manual*, Second Edition (1989) and Ausubel, et al., *Current Protocols in Molecular Biology* (1994–1997).

In a third step, for expression from the mutant U1 snRNA gene, the cell can be maintained under appropriate conditions (e.g., normal conditions for cell growth and cell division) for expression of the gene and production of the encoded mutant U1 snRNA. Generally, the cells are maintained in a suitable buffer and/or growth medium or nutrient source for growth of the cells and expression of the gene product(s). The growth media, which are not critical to the invention, are generally known in the art and include sources of carbon, nitrogen and sulfur. Examples include Dulbeccos modified eagles media (DMEM), RPMI-1640, M199 and Grace's insect media. The pH which can be selected is generally one tolerated by or optimal for growth of the cell.

As a particular example of the above approach to introducing mutant U1 snRNA into a cell, a gene encoding the mutant U1 snRNA can be integrated into the genome of a virus that enters the cell. By infection of the cell, the components of a system which permits the transcription and translation of the mutant U1 snRNA gene are introduced into the cell, in which expression of the encoded product occurs. Alternatively, an RNA polymerase gene, inducer, or other component required to complete such a gene expression system may be introduced into the cell already containing the mutant U1 snRNA gene, for example, by means of a virus that enters the cell and contains the required component. The mutant U1 snRNA gene can be under the control of an inducible or constitutive promoter. The promoter can be one that is recognized by the cell RNA polymerase. The promoter can, alternatively, be one that is recognized by a viral RNA polymerase and is transcribed following infection of the cell with a virus.

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses.

A DNA encoding a mutant U1 snRNA of the present invention can also be introduced into a cell by targeting the DNA to cell membrane phospholipids. For example, targeting of a DNA encoding a mutant U1 snRNA of the present invention can be accomplished by linking the DNA molecule to a VSV-G protein, a viral protein with affinity for all cell membrane phospholipids. Such a construct can be produced using methods well known to those practiced in the art.

A mutant U1 snRNA of the present invention can also be introduced into a cell in a liposome preparation or in another appropriate vehicle. The liposome preparation can be comprised of any liposomes which penetrate the stratum corneum and fuse with the cell membrane, resulting in delivery of the contents of the liposome into the cell. For example, liposomes such as those described in Yarosh, U.S. Pat. No. 5,077,211; Redziniak et al., U.S. Pat. No. 4,621,023; and Redziniak et al., U.S. Pat. No. 4,508,703 can be used. The teachings of these patents are incorporated herein by reference.

In addition, a mutant U1 snRNA of the present invention can be introduced into the cell by targeting the mutant U1 snRNA to a specific cell type. The mutant U1 snRNA that is targeted to a specific cell type can be a single-stranded RNA or a single-stranded chimeric RNA/DNA. Chimeric RNA/DNA molecules can be synthesized according to methods generally known in the art. For example, chimeric RNA/DNA can be synthesized by chemical synthesis.

Targeting of mutant U1 snRNA to a specifc cell type can be accomplished by a variety of methods known to those practiced in the art. For example, cells are typically characterized by markers expressed at their surface that are termed "surface markers". These surface markers include surface proteins or target molecules, such as cellular receptors, adhesion molecules, transporter proteins, components of the extracellular matrix and the like. These markers, proteins and molecules also include specific carbohydrates and/or lipid moieties, for example, conjugated to proteins. Thus, a chimeric mutant U1 snRNA-protein molecule which binds to one or more surface proteins on a target cell can be produced using methods well known to those skilled in the art. The chimeric mutant U1 snRNA-protein molecule can be comprised of a mutant U1 snRNA and a protein moiety which binds to one or more surface proteins on a target cell.

Surface proteins can be tissue- or cell-type specific (e.g. as in surface markers) or can be found on the surface of many cells. Typically, the surface marker, protein or molecule is a transmembrane protein with one or more domains which extend to the exterior of the cell (e.g. the extracellular domain). Where cell-type specific delivery is desired, the surface protein is preferably specific to the tissue. By "specific" to the tissue, it is meant that the protein be present on the targeted cell-type but not present (or present at a significantly lower concentration) on a substantial number of other cell-types. While it can be desirable, and even preferred, to select a surface protein which is unique to the target cell, it is not required for the claimed invention.

The surface protein can be a cellular receptor or other protein, preferably a cellular receptor. Examples of cellular receptors include receptors for cytokines, growth factors, and include, in particular epidermal growth factor receptors, platelet derived growth factor receptors, interferon receptors, insulin receptors, proteins with seven transmembrane domains including chemokine receptors and frizzled related proteins (Wnt receptors), immunoglobulin-related proteins including MHC proteins, CD4, CD8, ICAM-1, etc., tumor necrosis factor-related proteins including the type I and type II TNF receptors, Fas, DR3, DR4, CAR1, etc., low density lipoprotein receptor, integrins, and, in some instances, the Fc receptor.

Other examples of surface proteins which can be used in the present invention include cell-bound tumor antigens. Many of these surface proteins are commercially available and/or have been characterized in the art, including the amino acid and nucleic acid sequences, which can be obtained from, for example, GENBANK, as well as the specific binding characteristics and domains. Cytokine and chemokine receptors are reviewed for example, in Miyama, et al. *Ann. Rev. Immunol.*, 10:295–331 (1992), Murphy, *Ann. Rev. Immunol.* 12:593–633 (1994) and Miller et al. *Critical Reviews in Immunol.* 12:17–46(1992).

Typically, the protein moiety of the chimeric mutant U1 snRNA-protein molecule is selected or derived from native ligands or binding partners to the surface protein of the target cell. The protein moiety selected is one which results in delivery of the mutant U1 snRNA into the cell. The protein moiety can be a polypeptide comprising at least the receptor-binding portion of the native ligand. In one embodiment, the protein moiety is a polypeptide ligand to a cellular receptor. In a particular embodiment, the ligand is VSV-G protein. A "native ligand" or "native binding partner" is defined herein as the molecule naturally produced by, for example, the animal or species which binds to the surface protein in nature. Preferably, the protein moiety is a polypeptide or protein. As such, the native ligand of a cytokine receptor is the native cytokine. In another embodiment, the protein moiety can comprise a binding fragment of an antibody, such as the variable region or a single chain antibody.

Once in the cell, the mutant U1 snRNA is imported or translocated by the cell from the cytoplasm to the site of action in the nucleus.

The invention also includes nucleic acid molecules which encode the mutant U1 snRNA of the invention. The nucleic acid molecule can be double stranded or single stranded and can be a DNA molecule, such as cDNA or genomic DNA, an RNA molecule or a chimeric DNA/RNA molecule. The nucleic acid molecules can include expression control sequences (e.g., promoter sequences, enhancers, transcriptional binding sites). Nucleic acid molecules which encode the mutant U1 snRNA of the invention are described above.

Recombinant nucleic acid molecules which encode the mutant U1 snRNA of the invention include polymorphic or allelic variants, and portions (fragments) thereof, or variants of the naturally occurring genes. Such variants include mutants differing by the addition, deletion or substitution of one or more residues, modified nucleic acids in which one or more residues are modified (e.g., DNA or RNA analogs), and mutants comprising one or more modified residues.

Also envisioned are cells which comprise the nucleic acid molecules of the invention. Particular cells which comprise the nucleic acid molecules of the invention are discussed above.

The present invention also relates to methods of reducing expression of a gene in a human. In these methods, a mutant U1 snRNA which binds or hybridizes to a preselected site in a mRNA produced by a target gene (or DNA encoding the mutant U1 snRNA) is introduced into cells present in a biological sample obtained from an individual (e.g., blood, bone marrow). The cells can be migratory, such as a hematopoietic cell, or non-migratory, such as a solid tumor cell or fibroblast. After treatment in this manner, the sample is returned or readministered to (reintroduced into) the individual according to methods known to those practiced in the art. Such a treating procedure is sometimes referred to as ex vivo treatment. Ex vivo gene therapy has been described, for example, in Kasid et al., *Proc. Natl. Acad. Sci. USA,* 87:473 (1990); Rosenberg et al., *N. Engl. J. Med.,* 323:570 (1990); Williams et al., *Nature,* 310:476 (1984); Dick et al., *Cell,* 42:71 (1985); Keller et al., *Nature,* 318:149 (1985), and Anderson, et al. U.S. Pat. No. 5,399,346.

A series of treatments carried out in this manner can be used to prevent or inhibit the effects of an infectious agent. For example, blood can be removed from an individual infected with HIV or other viruses, from an individual with a dominant negative inherited disorder, or from an individual with cancer resulting from overexpression of a cancer gene. The blood can then be combined with a mutant U1 snRNA which binds or hybridizes to a preselected site in a mRNA produced by a target gene (or DNA encoding the mutant U1 snRNA) under conditions appropriate for entry into cells of the mutant U1 snRNA, binding or hybridization of the mutant U1 snRNA to the preselected site, and maintenance of the sample in such a condition that it can be returned or readministered to (reintroduced into) the individual. Where the mutant U1 snRNA is a ribozyme-U1 snRNA complex, the treated blood is also maintained under conditions appropriate for the selected ribozyme to cleave the mRNA produced by the targeted gene. In this aspect of the invention, the targeted gene is selected because its expression leads to undesirable and detrimental effects in the human (e.g., AIDS, dominant negative inherited disorder, cancer), thereby making it desirable to regulate, reduce or inhibit expression of the selected gene.

Alternatively, a mutant U1 snRNA (or DNA encoding the mutant U1 snRNA) can be administered to the patient. The mode of administration is preferably at the location of the target cells. As such, the administration can be nasally or by injection. Other modes of administration (parenteral, mucosal, systemic, implant, intraperitoneal, etc.) are generally known in the art. The mutant U1 snRNA (or DNA encoding the mutant U1 snRNA) can, preferably, be administered in a pharmaceutically acceptable carrier, such as saline, sterile water, Ringer's solution, and isotonic sodium chloride solution.

The dosage administered to an individual will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired.

In a particular embodiment, the method for treating and/or prophylaxis of a HIV infection further comprises introducing into the cells a mutant U1 snRNA which binds to a preselected site in the 3' LTR proximal to the polyadenylation site (the 3' terminal exon of the viral protein).

The present invention will now be illustrated by the following Examples, which are not intended to be limiting in any way.

EXAMPLES

Example 1

U1 Small Nuclear RNA Gene and Derivatives

Nucleic acid manipulations were preformed by standard procedures (Sambrook et al., Eds., *Molecular Cloning, A*

Laboratory Manual, 2nd edition, Cold Spring Harbor University Press, New York, 1989; and Ausubel et al., Eds., Current Protocols In Molecular Biology, John Wiley & Sons, New York, 1994–1997).

The parent phU1 construct (Lund et al., *J. Biol. Chem.*, 259(3):2013–2021 (1984), consisting of the human U1 promoter and gene, was cloned into the pUC19 cloning vector within the EcoRI and HindIII restriction sites using standard cloning methods. A map of the U1 snRNA construct is presented in FIG. 1.

The human U1 snRNA derivatives (mutant U1 snRNA) used to reduce expression in cells of the CAT, eGFP and β-gal genes (target reporter constructs) were made through polymerase chain reaction (PCR) based mutagenesis as described in Deng et al.,*Anal. Biochem.*, 200:81–88 (1992)). Briefly, mutations (shown in bold) in the antisense portion of the U1 gene were incorporated into the 5' oligonucleotide starting with the BglII restriction endonuclease site underlined below.

```
            BglII                       (SEQ ID NO:3)
              |
5'-GGCCCAAGATCTCATACTTACCTGGCAGG-3'
5'hU1 sequence BglII                       (SEQ ID NO:4)
              |
5'-GGCCCAAGATCTCAGATGAACCTGGCAGG-3'
5'U1:CAT 570 primer
```

The 3' oligonucleotide beginning with HindIII (underlined) was used for selection of the mutant PCR product by elimination of a PstI restriction endonuclease site (underlined, with mutation in bold) within the pUC19 multiple cloning site as shown below.

```
       HindIII      PstI               (SEQ ID NO:5)
          |          |
5'-CAGTGCCAAGCTTGCATGCCTGCAGGTC-3'
3'hU1 sequence HindIII      ΔPstI              (SEQ ID NO:6)
          |          |
5'-CAGTGCCAAGCTTGCATGCCAGCAGGTC-3'
3'Universal ΔPstI selection primer
```

The resultant double stranded PCR product was digested with BglII/HindIII and subsequently ligated to a BglII/HindIII digested parent hU1 construct. The clones were screened for the loss of the PstI site by restriction analysis using standard methods and sequenced to confirm the mutation. Sequencing was done using an ABI373 fluorescent sequencer (Perkin Elmer, Norwalk, Conn.).

Figure 2:
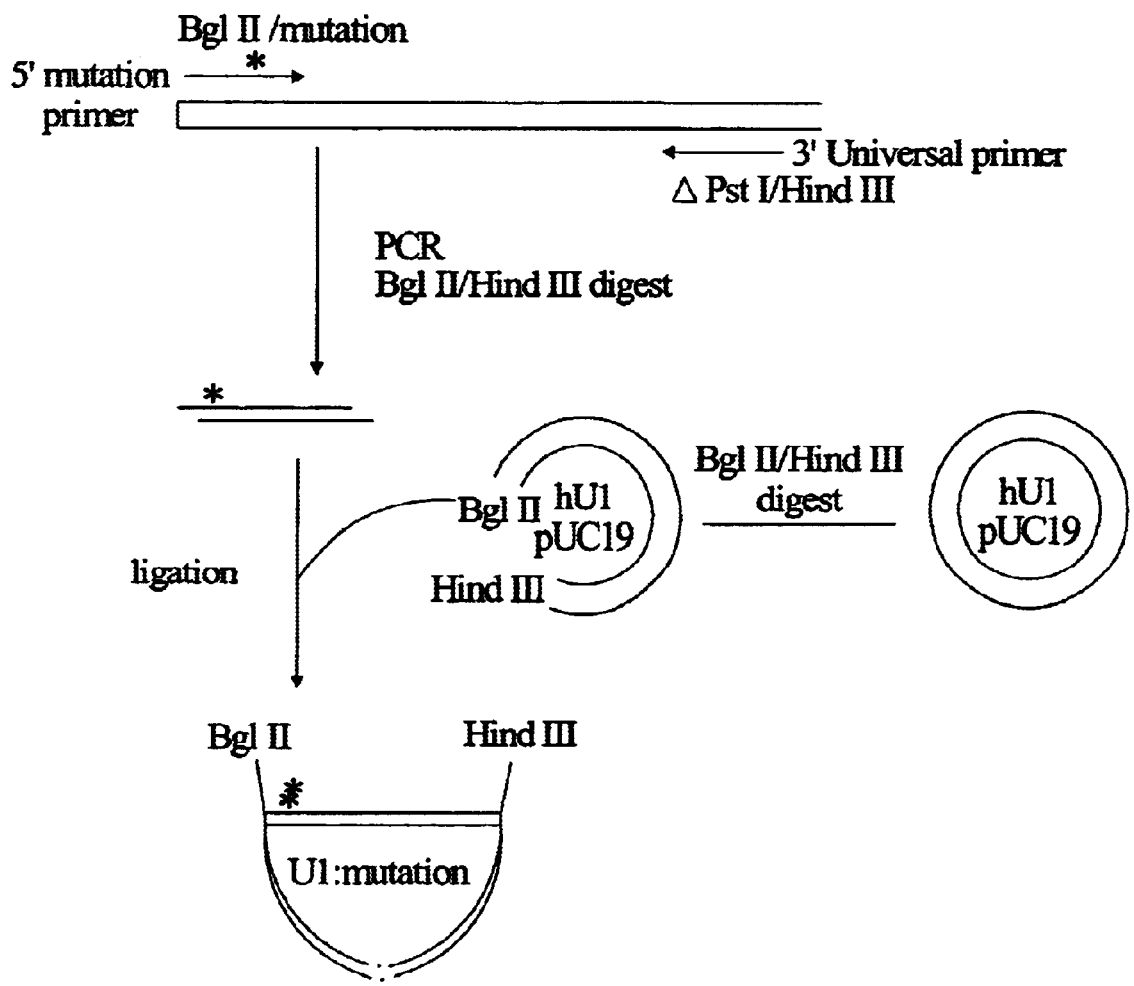
FIG. 2 is a schematic diagram outlining the method used to produce the U1 snRNA derivatives (mutant U1 snRNAs) used to reduce expression of the CAT, eGFP and β-gal genes in cells.

A schematic diagram outlining the method used to produce the U1 snRNA derivatives (mutant U1 snRNAs) used to reduce expression in cells of the CAT, eGFP and β-gal genes (target reporter constructs) is presented in FIG. 2. A schematic representation of human U1 snRNA construct and the sequence changes made to produce the U1 derivatives (mutant U1 snRNAs) used to reduce expression in cells of the CAT, eGFP and β-gal genes (target reporter constructs) is presented in FIG. 3.

Example 2

Expression Vectors

Nucleic acid manipulations and plasmid preparation were preformed by standard procedures (Sambrook et al., Eds., *Molecular Cloning, A Laboratory Manual*, 2nd edition, Cold Spring Harbor University Press, New York, 1989; and Ausubel et al., Eds., *Current Protocols In Molecular Biology*, John Wiley & Sons, New York, 1994–1997).

Figure 3:
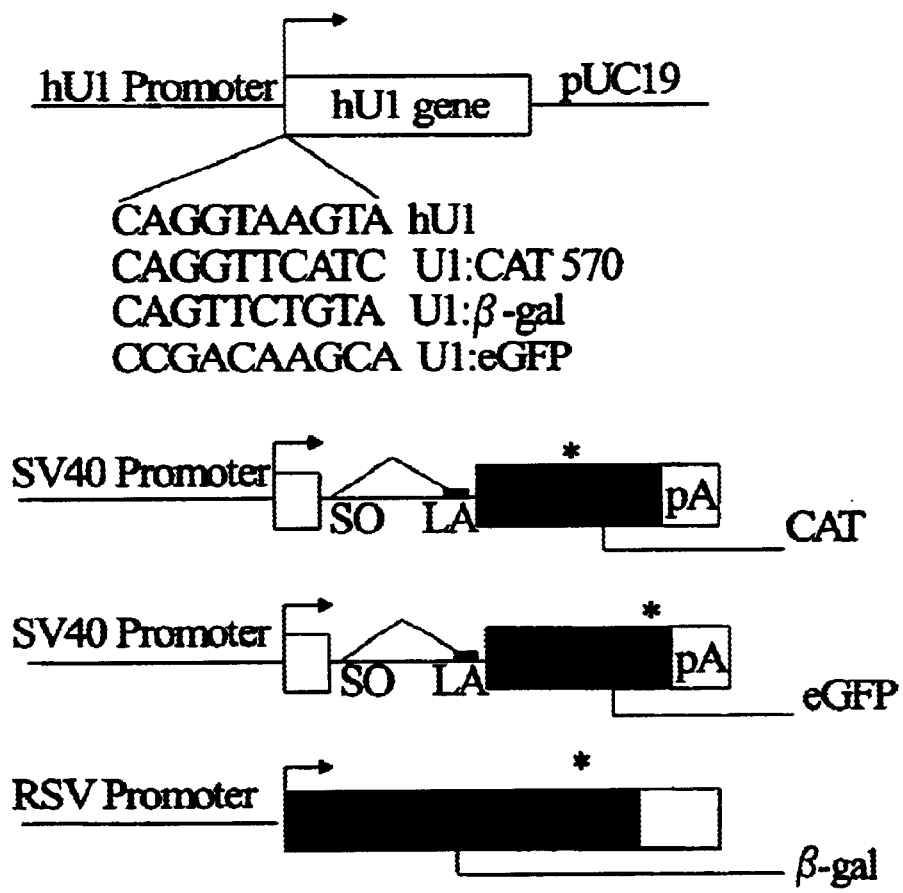
FIG. 3 is a schematic representation of a human U1 snRNA construct (hU1) and the sequence changes made to obtain the U1 derivatives (mutant U1 snRNAs) used to reduce expression of the CAT, eGFP and β-gal genes in cells. DNA sequences from hU1 and the U1:CAT 570, U1:β-gal and U1:eGFP constructs are shown (SEQ ID NOs: 2, 7, 8 and 9, respectively).

In vivo, chloramphenicol acetyltransferase (CAT) and enhanced green fluorescent protein (eGFP) reporter genes were expressed from vectors that contained a eukaryotic promoter followed by a splice donor-acceptor unit. Specifically, the CAT expression vector pOB4CAT is driven by the simian virus 40 (SV40) early promoter and contains a 1500-bp intron (SD=splice donor; SA=splice acceptor) upstream of the CAT coding sequence as shown in FIG. 3. The 200-bp 3'UTR contains the SV40 early polyadenylation signal.

The expression vector pOB4eGFP was produced by replacing in the pOB4CAT expression vector, the XbaI-XhoI fragment containing the CAT gene with a XbaI-XhoI fragment containing the eGFP gene (Clonetech, California). This expression vector contains a 1500-bp intron (SD=splice donor; SA=splice acceptor) upstream of the eGFP coding sequence as shown in FIG. 3. The 200-bp 3'UTR contains the SV40 early polyadenylation signal.

Figure 4:
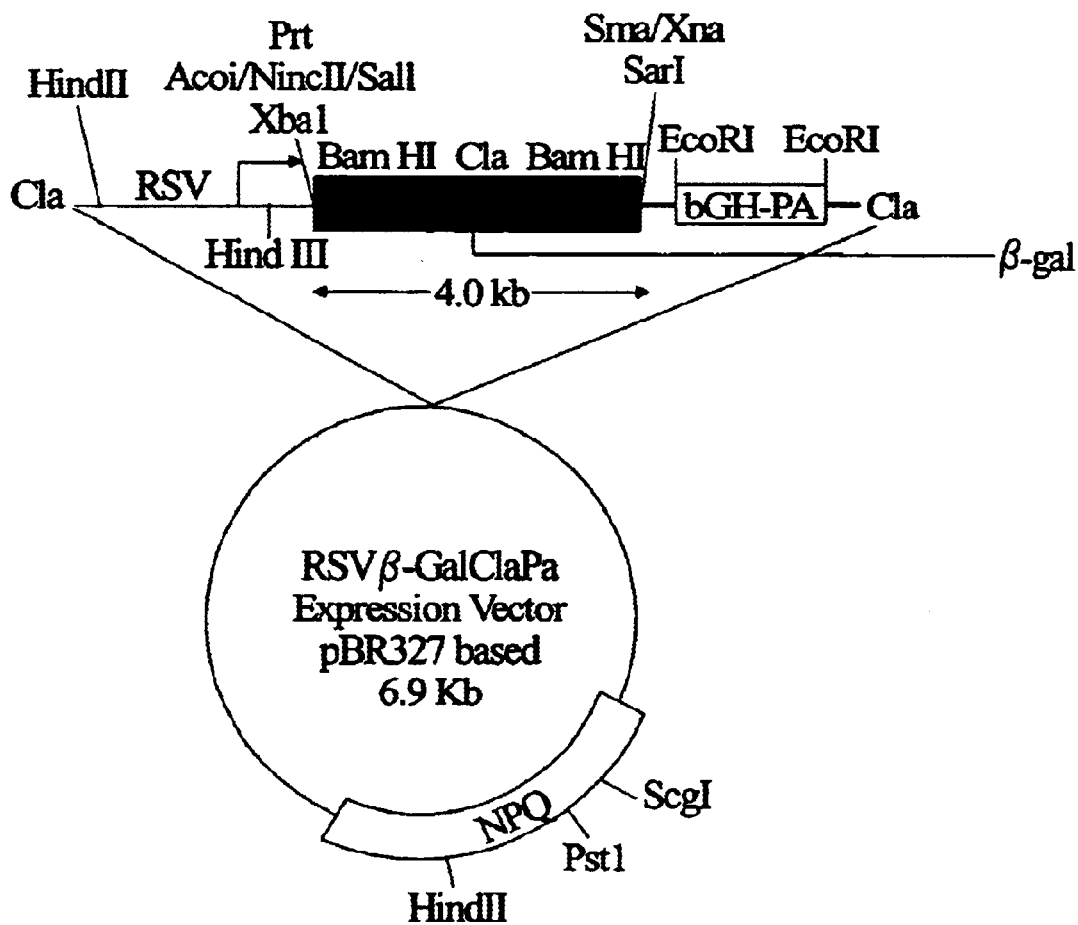
FIG. 4 is a genetic map of the expression vector RSV β-GalClaPa.

The expression vector RSV β-GalClaPa contains the RSV promoter and β-gal gene in a pBR327 vector. A map of this expression vector is presented in FIG. 4. The components used in constructing this expression vector are widely available to those skilled in the art.

The presence of a splice donor-acceptor unit in the pOB4CAT and pOB4eGFP expression vectors made it necessary for these reporter constructs to go to U1 snRNA associated splicing domains prior to their export to the cytoplasm.

The β-gal reporter was expressed without a splicing event to determine if the U1 targeting system could reduce the output from intronless genes.

The modified U1 snRNA was targeted to the terminal exon of reporter constructs to cause nuclear retention of the target mRNA (Furth et al., *Mol. Cell. Biol.*, 14(8):5278–5289 (1994)).

Example 3

Cells and Transfection

The NIH3T3 cell line (American Type Tissue Collection, Bethesda, Md.) was maintained in Dulbecco's modified Eagle medium supplemented with 10% fetal calf serum.

NIH3T3 cells were transfected with DNA by the calcium phosphate method as described in Gorman et al., *Science*, 221:551–553 (1983). The total DNA within the precipitate was 10 μg and the weight ratio of the test DNA to the selector DNA (neomycin or hygromycin) was 10:1.

Transient assays were performed 2 days after cells were manipulated. The introduced DNA persisted in the cell for about 3 to 4 days and then was degraded by the cell.

In a stable transfection, the relatively small number of cells that incorporated the introduced DNA into their chromosomes were obtained by selection with a second gene (selectable marker gene, such as neomycin or hygromycin) which was included in the transfection mixture (test gene and selector gene).

Transient assays assess a gene without the gene being incorporated into the cell chromosome. In contrast, in stable transfections, the gene is incorporated into the cell chromosome.

Example 4

Assays for Chloramphenicol Acetyltransferase, β-galactosidase and Enhanced Green Fluorescent Protein Expression CAT activity was measured as described in Gorman et al., *Mol. Cell. Biol.*, 2:1044–1051 (1982) and was normalized to the expression of luciferase (Promega, Madison, Wis.) using Promega reporter assay lysis buffer (Promega, Madison, Wis.) and the lucerferase assay system according to the manufacturer's instructions (Promega, Madison, Wis.).

β-gal expression was quantitated by cell count of transiently transfected cells.

eGFP protein expression was quantitated by fluorescent activated cell sorting (FACS) analysis of transiently and stably transfected cells.

Example 5

RNA Isolation and Northern Blotting

Total cellular RNA was isolated 2 days after transfection using the Tri-reagent RNA extraction protocol according to manufacturer's instructions (Life Technolgies Inc., Grand Island, N.Y.). Briefly, RNA was fractionated on a 6–7% formaldehyde, 1% agarose gel for 3 hours at 85–90V. The RNA was transferred to S&S nylon membranes (Schleicher & Schuell, Inc., Keene, N.H.) and hybridized with random primed α-$^{32}$PdCTP (New England Nuclear, Massachusetts) labelled CAT, eGFP or β-gal DNA probes. See also Chomczynski et al., Anal. Biochem., 162:156–159 (1987).

Example 6

Efficacy of U1 Small Nuclear RNA as an Antisense Vehicle

To assess the efficacy of U1 snRNA as an antisense vehicle, a U1 snRNA gene was engineered to complement bases 570–578 of the chloramphenical acetyl transferase (CAT) coding sequence (Alton et al., Nature, 282:864–869 (1979); GenBank accession no. V00622J01841) (U1:CAT 570) as described in Example 1.

NIH3T3 cells were transiently co-transfected with 5 µg of the U1:CAT 570 construct and 5 µg of the pOB4CAT expression vector as described in Example 3. As a control, NIH3T3 cells were transfected with 5 µg of an unmodified human U1 (hU1) construct and 5 µg of the pOB4CAT expression vector as described in Example 3. CAT RNA and protein levels were determined as described in Examples 4 and 5.

Figure 5:
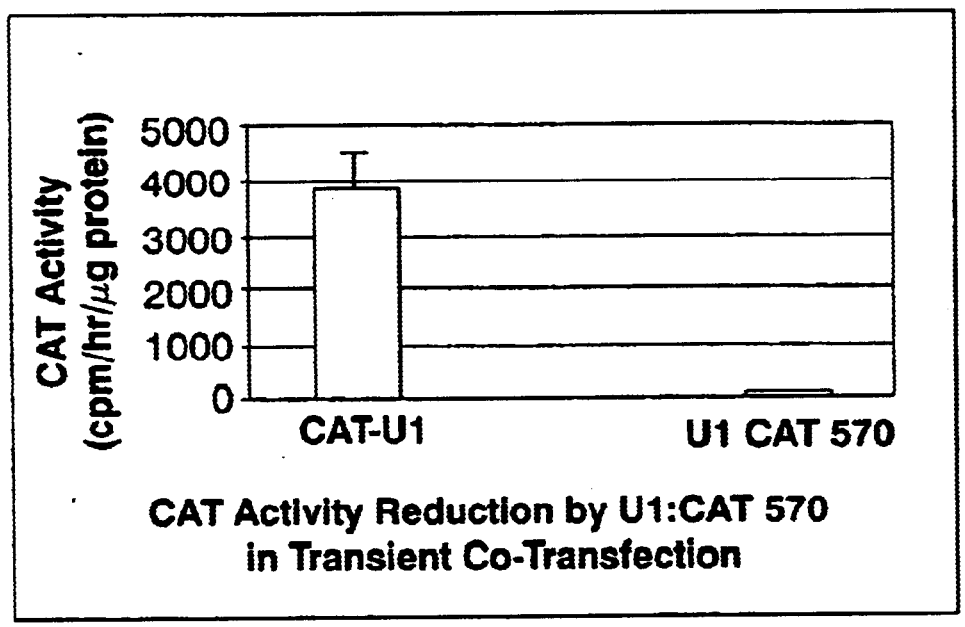
FIG. 5 is a bar graph showing the reduction in chloramphenicol acetyltransferase (CAT) activity in the cell lysates of NIH3T3 cells transiently co-transfected with 5 μg of the U1:CAT 570 construct and 5 μg of the pOB4CAT expression vector.

Cytoplasmic CAT enzyme activity, normalized to luciferase activity, was reduced to 5–10% compared with unmodified U1 transfected controls (FIG. 5). Quantitation of CAT RNA from northern blot analysis showed a corresponding decrease to ≦10% when compared with controls.

Example 7

Reduction of Enhanced Green Fluorescent Protein and β-galactosidase Reporter RNA and Protein Levels in Transiently Co-Transfected NIH3T3 Cells To determine the degree to which gene expression was reduced within individual cells and to test whether the U1 snRNA mediated gene reduction was limited to CAT, the hU1 gene was modified to recognize two other reporter genes, eGFP and β-gal. The hU1 gene was modified as described in Example 1 to yield the U1:eGFP and U1:β-gal genes.

In independent experiments, NIH3T3 cells were transiently co-transfected with either 5 µg of the U1:eGFP construct or 5 µg of the U1:β-gal construct and 5 µg of its target construct (either pOB4eGFP or RSV β-GalClaPa) as described in Example 3. As a control, NIH3T3 cells were co-transfected with 5 µg of an unmodified hU1 construct and 5 µg of the appropriate target construct (either pOB4eGFP or RSV β-GalClaPa) as described in Example 3. eGFP and β-gal RNA and protein levels were determined as described in Examples 4 and 5.

The results from each experiment showed that U1:eGFP and U1:β-gal reduced eGFP and β-gal mRNA levels respectively by 90%.

Staining for eGFP showed that the total number of cells expressing eGFP were dramatically reduced by U1:eGFP. Staining for β-gal also showed that the total number of cells expressing β-gal protein were decreased by U1:β-gal.

Example 8

Reduction of Cat RNA and Protein Levels in Stably Co-Transfected NIH3T3 Cells

To more closely assess the activity of U1:CAT 570 within individual cells, stably transfected cell lines of the CAT and cognate U1 genes were generated and selected as described in Example 3.

Clonal cell populations were assayed for the presence of CAT and/or U1:CAT 570 transgenes as described in Example 4.

Figure 6:
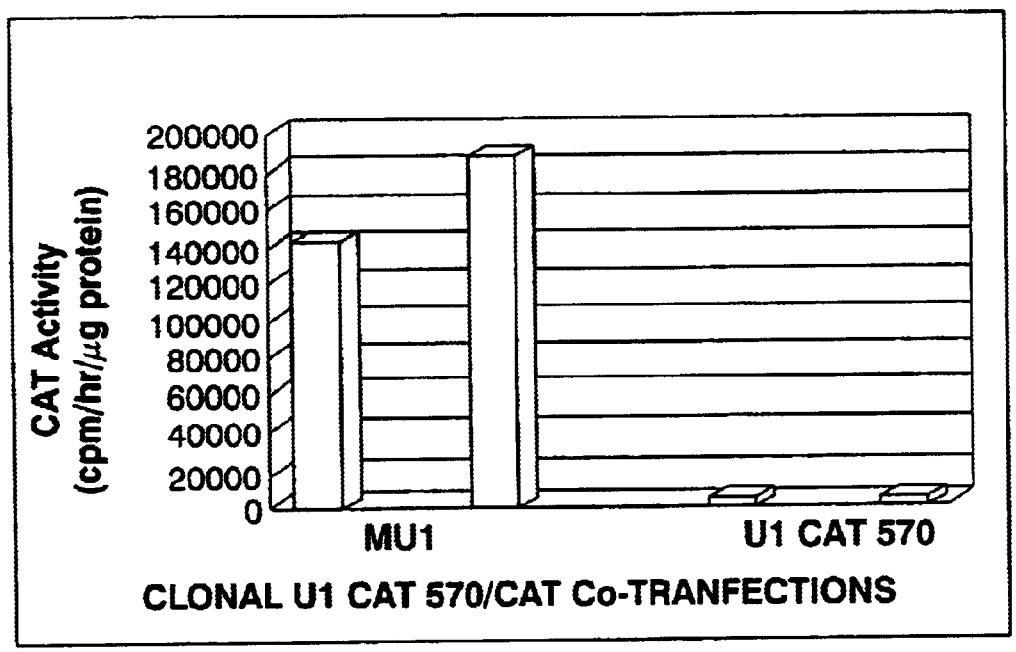
FIG. 6 is a bar graph showing the reduction in CAT activity in the cell lysates of NIH3T3 cells stably co-transfected with 5 μg of the U1:CAT 570 construct and 5 μg of the pOB4CAT expression vector.

The CAT activity was reduced by more than 99% in 4 independently assayed clones containing the complementary U1 snRNA when compared to controls with hU1. Two representative clones from each population are shown in FIG. 6. These results show that once U1 snRNA targeted to an mRNA is expressed in a cell, it completely reduces gene expression.

Example 9

Specificity of U1 Targeting Constructs

To test the specificity of the U1 targeting constructs for cross-reactivity with other RNAs, the levels of a second reporter gene included in transient co-transfection experiments were analyzed. Endogenous and modified U1 snRNAs can recognize splice donor sites with up to 2 mismatched bases and still participate in splicing (Cohen et al., Mol. Cell. Biol., 13:2666–2676 (1993)). This suggests that a modified U1 snRNA targeted to one gene may bind nonspecifically to RNA sequences from other genes. This lack of specificity would be undesirable in analyzing the function of a single gene.

NIH3T3 cells were transfected with a combination of eGFP and β-gal expression vectors and either hU1 or U1:β-gal as described in Example 3. Cells marked as eGFP expressors were subsequently stained for the presence of β-gal by standard methods well known to those practiced in the art. eGFP and β-gal RNA and protein levels were determined as described in Examples 4 and 5.

The control cells transfected with unmodified hU1 were positive for expression of both transgenes but cells transfected with U1:β-gal showed predominately eGFP expression. The converse experiment was performed with U1:eGFP in place of U1:β-gal. Total RNA was harvested. The results confirm that high levels of U1 snRNA targeted to a gene have specifically reduced its protein expression. The results of these experiments clearly indicate that U1 snRNA altered only the levels of RNA expressed from the targeted gene. These data suggest that the U1 transgenes are not promiscuous and associate only with their target mRNA. The ability to generate stably transfected cells show their tolerance of exogenous U1 snRNA transcripts.

Example 10

RNA Partitioning of the Target Following U1 Targeting

U1 snRNA follows a maturation process common to all splicing associated snRNAs with the exception of U6 snRNA. The U1 snRNA transcript is exported to the cytoplasm where is associates with the protein sub-units which comprise U1 snRNP. This U1 snRNA/snRNP complex returns to the nucleus in foci coincident with the SC-35 non-essential splicing factor (Huang et al., *Proc. Natl. Acad. Sci. USA*, 89:305–308 (1992); Romac et al., *Mol. Cell. Biol.*, 14:4662–4670 (1994); Marshallsay et al., *EMBO J.*, 13:222–231 (1994); Grimm et al., *Nucleic Acids Symp. Series*, 34–36 (1995); Grimm et al., *EMBO J.*, 16:793–806 (1997); and Fischer et al., *J. Cell Biol.*, 125:971–980 (1994)). Lawrence and coworkers demonstrated that, concurrent with transcription, pre-mRNA proceeds directly into SC-35 domains adjacent to the locus of transcription (Xing et al., *J. Cell Biol.*, 131:1635–1647 (1995)). U1 RNA interacts with pre-mRNA to initiate splicing in these SC-35 domains. It is reasonable to expect that it is here that a modified U1 RNA will interact with its target.

The transgenic U1 snRNA described herein was localized primarily in the nucleus by reverse transcriptase-polymerase chain reaction (RT-PCR) analysis of differentially extracted nuclear and cytoplasmic RNA as previously described by Redford-Badwal et al. (*J. Clin. Invest.*, 97:1035–1040 (1996)). This suggested that the transgenes follow the predetermined cell trafficking pattern and will home to SC-35 domains where they can bind to splicing mRNA species with sequence complementary to the U1 snRNA antisense domain.

In control cells transfected with hU1 and CAT genes, although some CAT mRNA was observed in the nucleus, most of the CAT mRNA was observed in the cytoplasm. Further, following additon of U1:CAT 570, CAT mRNA was observed largely in the nucleus. These results suggest that targeting U1:CAT to a coding sequence of a message inhibits its processing and impedes its export from the nucleus.

Example 11

Analysis of Polyadenylation in Target RNA

The mechanism for U1 snRNA mediated nuclear retention of the target may be a direct result of interference, as with unpaired donor sites, or an indirect result of interference with polyadenylation of the message. In evaluating the mechanism of U1 snRNA mediated nuclear retention of the target, the ratio of polyadenylation between the nuclear retained messages of experimental and control groups was examined. RNase protection assays (Sambrook et al., Eds., *Molecular Cloning, A Laboratory Manual*, 2nd edition, Cold Spring Harbor University Press, New York, 1989; and Ausubel et al., Eds., *Current Protocols In Molecular Biology*, John Wiley & Sons, New York, 1994–1997) on the experimental groups show no difference in the amount of polyadenylation from controls, suggesting that U1 snRNA uses a more direct manner of inhibition.

Equivalents

Those skilled in the will recognize or be able to ascertain using no more than routine experimentation, many equivalents to the specific embodiments of the invention described herein. Such equivalents are intended to be encompassed by the following claims.

---

What is claimed is:

1. A nucleic acid construct comprising a U1 snRNA, wherein the U1 snRNA is modified so that it is complementary to a preselected nucleotide sequence in a target nucleic acid, wherein the preselected nucleotide sequence is in a terminal (3') exon of the target nucleic acid, said U1 snRNA being modified at a 5' end to render the construct complementary to the preselected nucleotide sequence.

2. The nucleic acid construct of claim 1, wherein the first 10 nucleotides at the 5' end of the U1 snRNA are modified to render the construct complementary to the preselected nucleotide sequence.

3. The nucleic acid construct of claim 1, wherein the modified U1 snRNA does not bind to SEQ ID NO: 2.

* * * * *